United States Patent [19]

Wilson

[11] 4,041,180
[45] Aug. 9, 1977

[54] INTRODUCING GASES INTO FERMENTATION LIQUIDS

[75] Inventor: Richard John Hugh Wilson, Copthorne, England

[73] Assignee: Brewing Patents Limited, London, England

[21] Appl. No.: 664,352

[22] Filed: Mar. 5, 1976

[30] Foreign Application Priority Data

Apr. 8, 1975  United Kingdom ............... 14461/75

[51] Int. Cl.² .......................... C12C 11/00; C12B 1/14
[52] U.S. Cl. ........................................ 426/11; 426/15;
426/16; 426/474; 426/475; 195/95; 195/109;
195/142
[58] Field of Search .......................... 195/109, 95, 142;
426/11, 15, 16, 474, 477, 330, 475

[56] References Cited

U.S. PATENT DOCUMENTS

| 3,041,250 | 6/1962 | Wolnak | 195/109 |
|---|---|---|---|
| 3,123,475 | 3/1964 | Wendt et al. | 426/16 |
| 3,345,179 | 10/1967 | Pollock et al. | 426/16 |
| 3,506,460 | 4/1970 | Bayne | 426/330 |
| 3,698,913 | 10/1972 | Malinin | 426/474 |
| 3,723,255 | 3/1973 | Walden et al. | 195/109 |
| 3,850,753 | 11/1974 | Chibata et al. | 195/109 |

*Primary Examiner*—Alvin E. Tanenholtz
*Assistant Examiner*—C. A. Fan
*Attorney, Agent, or Firm*—Wenderoth, Lind & Ponack

[57] ABSTRACT

The bubbling of poorly soluble gases into fermentation liquids either for the replenishment of dissolved oxygen or for removal of excess super-saturated $CO_2$ can lead to severe foaming problems, particularly in deep fermentation vessels. The present invention overcomes this problem by dissolving the gas in an aqueous medium, usually water, under superatmospheric conditions and injecting the gas solution into the fermentation liquid in controlled quantities under conditions such that the gas is either retained in solution in the fermentation liquid or, at most, the gas is released from solution in the form of microbubbles of much smaller size than can be obtained by passing gas through a porous diffuser. Microbubbles may be released from the gas solution by injecting the pressurized gas solution into the fermentation liquid under conditions of high shear rate.

10 Claims, 5 Drawing Figures

INTRODUCING GASES INTO FERMENTATION LIQUIDS

The present invention relates to the introduction of gases into a liquid in which the gas is relatively insoluble, i.e., has a solubility of less than 1% by weight when the liquid is saturated with gas at atmospheric pressure and at the temperature at which the gas is to be introduced into the liquid.

The invention is particularly although not exclusively applicable to fermentation processes. In many liquid fermentation processes it is necessary or desirable to introduce a poorly soluble gas or mixture of gases into the fermentation liquid either before and/or during and/or after the period of fermentation itself.

A particular application of the invention is the introduction of air or oxygen or other relatively insoluble gas or gases into wort in brewing beer.

Another application of the invention is to the introduction of such a gas into a fermentation liquid in the form of very fine bubbles for the purpose of reducing the level of dissolved carbon dioxide.

In the fermentation of brewers wort, particularly in fermentation processes carried out in deep fermentation vessels, the introduction of oxygen into the wort is required to maintain the yeast in an active condition.

Current processes for introducing oxygen into wort involve sparging the gas into the liquid whilst it is in a tank or pipeline in such a way as to effect direct contact between gas and liquid. Sparging involves passing the gas for instance through a conduit with a perforated wall so that the gas bubbles through into the liquid. The gas will then dissolve in the liquid provided that the liquid is not already saturated with the gas. As an alternative the gas may be forced into solution by containing the liquid in a closed tank having a head space of gas which may be at any pressure at or above atmospheric pressure. Air can also be introduced into wort as it is poured into a fermentation vessel or through the open top of the fermenting vessel if it is of the type which is not closed. Generally therefore the introduction of gas into the fermentation liquid is achieved by direct contact of the gas with the fermentation liquid.

Where methods using direct contact of liquid and gas are employed it is usual for gas bubbles to rise through the liquid to the surface and cause an undesirable foam. This is wasteful of oxygen and it is quite usual for 90% of the gas to be lost in this way unless vigorous stirring is employed. Another drawback of direct contact methods is that it is difficult to introduce oxygen and at the same time collect and recover carbon dioxide given off during the fermentation. Carbon dioxide is quite commonly collected for use in other applications, but for that purpose, it must be of good purity.

The bubbling and foaming problems referred to are particularly acute in fermentation of wort where the wort has a high specific gravity and the bubbles create voluminous foam which wastes space in the fermentation vessel. Where oxygen is bubbled into high specific gravity worts during fermentation, then the problems which arise are particularly acute and have necessitated the undesirable addition of an anti-foaming agent.

In many fermentation processes the liquor becomes supersaturated with carbon dioxide and it becomes desirable to reduce the level of dissolved carbon dioxide during and/or after fermentation.

In the brewing of beer it is common for a fermenting wort to contain carbon dioxide in such an excess over the amount required for saturation that the fermenting liquid is in a highly unstable state. In this condition any mechanical shock transmitted to the fermenting liquid is liable to precipitate sudden release of a part of the excess gas in the form of a multitude of bubbles, which may form so large a volume of foam that it cannot be contained within the fermentation vessel. If prior allowance is made for such an occurence then the effective working capacity of a given vessel must be reduced to provide the extra space for the foam to expand into.

At the end of a fermentation it may be desirable to reduce the dissolved $CO_2$ content in the fermented liquid. In a brewery it often happens that the $CO_2$ content of the beer after fermentation is higher than that required for the product beer. This is particularly a problem when the fermentation has been carried out in deep vessels such as the cylindro-conical fermenters found in many modern breweries. It is well known that the level of dissolved carbon dioxide found in a wort of the end of fermentation is generally higher when the fermentation is conducted in such vessel than it is when the wort is fermented in a relatively shallow vessel.

Methods currently available for reducing the gas content of fermentation liquids are crude. Typically, the level of dissolved $CO_2$ in a brewery fermentation may be reduced by bubbling a gas such as nitrogen into the fermentation liquid via a gas diffuser made of a porous material such as sintered ceramic. Dissolved carbon dioxide diffuses into the rising gas bubbles and in this way carbon dioxide is swept out of the liquid. However, this process is somewhat wasteful because the gas bubbles released from the diffuser are usually of the order of 1 mm diameter and rise rapidly through the fermentation liquid. Shock waves may be set up by the gas entering the fermenter, especially if the gas is blown in through an open pipe instead of a diffuser, and these waves may cause spontaneous and uncontrolled formation of $CO_2$ bubbles in the bulk of the fermentation liquid. This is most likely to happen if the fermentation is vigorous and can be dangerous in a closed vessel.

It is one object of the present invention to provide a procedure for introducing oxygen into a fermentation liquid in such a manner as to avoid the formation of excessive foam in the fermentation vessel and to achieve economy in the use of oxygen.

It is another object of the invention to effect a control of the dissolved carbon dioxide content of a fermentation liquid and to remove excess carbon dioxide therefrom in a gentle manner to avoid the uncontrolled rapid release of carbon dioxide therefrom.

By a fermentation liquid is meant a liquid which is to be or has been fermented or is fermenting. The invention is particularly applicable to beer-brewing wort, although it may find application in wine-making or other similar processes. The chief gas used will be oxygen, either in air or preferably pure, although nitrogen or other gases can be introduced in this way. Nitrogen for instance can be introduced at some stage to stabilize foam in the finished beer.

To achieve these purposes oxygen or other poorly soluble gas is introduced into the fermentation liquid in the form of a gas solution, which is highly supersaturated in relation to the temperature and pressure conditions within the body of fermentation liquid. The supersaturated solution of poorly soluble gas is produced by dissolving the gas in a carrier liquid under superatmospheric pressure. Depending on the manner and quantity in which the pressurized gas solution is introduced into the fermentation liquid, the dissolved gas may be retained in solution or may be released from the solution in the form of microbubbles, which act as nuclei for the release of carbon dioxide from the fermentation liquid. In both cases the sudden release of carbon dioxide and the rapid generation of foam is avoided.

The solution of poorly soluble gas may be introduced into the fermentation liquid in several ways. One method of introduction involves vigorous injection of the solution at high pressure into the low pressure fermentation liquid, so that rapid pressure drop occurs concomitant with effective mixing of the liquids. In a second method the gas solution is mixed with fermentation liquid in a suitable proportion at a superatmospheric pressure and then the pressure is reduced to that of the bulk of the fermentation liquid. In the first case gas bubble formation is prevented or restricted by allowing insufficient time either for bubbles to form spontaneously at all or to grow significantly if they do form, before the gas is diluted to a concentration below its saturation value at the pressure of the mixed liquids in the fermentation vessel. In the second case the liquids are mixed before introduction into the fermentation vessel to achieve dilution and then the pressure is reduced so that again little or no bubble formation occurs.

As has been mentioned, the invention is particularly applicable for oxygenating wort, and problems currently exist with this step. The oxygenation of high specific gravity wort during fermentation by bubbling oxygen or air into the fermentation vessel leads to foaming problems which are very difficult to overcome (except by addition of anti-foaming agents) and are also characterized by a certain unpredictability.

The present invention when applied to oxygenating wort can reduce or eliminate these problems, due to the greatly reduced volume bubbling of gas introduced in the form of bubbles. Also, with the invention, it is possible to oxygenate at a slow rate over a prolonged time, which is particularly advantageous with high specific gravity worts during fermentation where most acute foaming may occur. This increases the possibility of satisfactory fermentation at high specific gravity by allowing successful oxygenation during fermentation, thus assisting in keeping the yeast active and alive.

A further advantage of this application of the invention is that with high specific gravity wort, oxygenation carried out during fermentation reduces the ester level in the fermented wort and this allows some control of flavour, reducing another obstacle to high specific gravity fermentation where the beer is subsequently to be diluted.

The introduction of the oxygen or air solution can be closely controlled over a long period of time so that small amounts of oxygen may be quantitatively delivered without substantial bubble formation. Thus it is possible for fermentation vessels to have only as much oxygen within them as is needed to keep the yeast in a suitable metabolic state. Thus it may be appropriate to have repeated slow injections of oxygen solution, for instance lasting 2 to 4 hours at intervals during fermentation or even over periods of one or two days towards the end of fermentation to reduce the ester level. Alternatively more frequently repeated injections of shorter duration could be used.

The advantages of the slow addition of oxygen which the invention allows lie in the reduced gushing or foaming which follows the formation of gas bubbles, the reduction of oxygen loss due to sweeping out by generated carbon dioxide, a probable reduction in unpleasant flavours due to oxidisation and a quicker dissolution of oxygen in the wort.

Where oxygen is to be introduced into wort with the invention it is preferred to introduce an oxygen solution rather than air solution as approximately five times as much oxygen can be introduced into the wort for a given amount of carrier liquid in this way. Obviously, for a given amount of oxygen difficulty might be encountered if the dilution rate of the wort were increased five-fold.

With all gases it may be advantageous for the gas solution carrier liquid to be cooled to below ambient atmospheric temperature, for instance to 2° C, as at this temperature about 50% more gas can be dissolved in the carrier liquid than at 18° C, irrespective of pressure. Against the resultant saving in oxygenation plant size will have to be considered the difficulties of conveying the cold liquid and keeping it cold as it is transported to fermentation vessels. In addition difficulties in injecting the oxygenated carrier liquid may be encountered as it is likely to warm up as it reaches the injection point in the fermentation vessel.

A typical brewery wort may contain about 6 ppm oxygen, that is about 1 grm. oxygen per barrel (36 Imperial gallons) of wort prior to fermentation. If oxygen is dissolved in water at 2° C and 1 atmosphere pressure, there is 0.066 grms/liter oxygen in the water, or at 5 atmosphere pressure there is 0.32 grms/liter. To give 1 grm. oxygen per barrel one therefore requires 15.2 liters of water per barrel if oxygenated at 1 atmosphere, and 3.1 liters per barrel if oxygenation at 5 atmospheres giving respective dilution rates of 9.3% and 1.9%. A similar oxygen requirement over a long period, for instance between 2 and 48 hours, towards the end of fermentation may be needed with high specific gravity worts to reduce ester levels.

Thus it may be said that in carrying out oxygenation of wort by the method of the invention the oxygen should be dissolved in aqueous solution under a pressure of at least 3 atmospheres and preferably 5–10 atmospheres or even up to 20 atmospheres and at a temperature up to 25° C, more preferably 2°–18° C.

Where the invention is employed for the degassing of a fermentation liquid instead of or in addition to the introduction of oxygen for stimulation of yeast, the gas solution is introduced so as to give rise to microbubbles on release into the fermentation liquid in the fermentation vessel. These microbubbles are about an order of magnitude smaller in diameter than the bubbles produced by a fine ceramic diffuser. They are much more economical and efficient as a means for removing dissolved gas, since they rise more slowly and have a much larger surface-to-volume ratio. In consequence the ratio between the volume of a microbubble and the $CO_2$ removed thereby is far higher than in the case of larger bubbles. The process is moreover gentler because the final bubble size is smaller than in prior art arrangements. The microbubbles are generated by allowing the pressurized gas solution to be passed through a nozzle under conditions such that the pressure on the ejecting liquid is suddenly dropped with the promotion of a high degree of liquid shear which causes the precipitation of a proportion of the dissolved gas in the form of the microbubbles. Typically, the gas used may be air, oxygen, nitrogen or carbon dioxide.

By the introduction of oxygen or air in small volume in the form of microbubbles through the whole or a large part of the fermentation period it is possible to avoid the build-up of carbon dioxide supersaturation normally encountered in brewing in deep fermentation vessels.

Microbubbles of air in water can readily be formed by passing water which has been saturated with air at ambient temperature at about 5 atmospheres absolute pressure, through a needle valve opening to 1 atmosphere pressure. A rapid drop in pressure which occurs, together with a high degree of shear, causes the release of a large part of the dissolved gas in the form of microbubbles and gives the liquid in a milky appearance. The majority of these bubbles leaving the valve are believed to have diameters in the range 20-120 micrometers but it must be appreciated that, in degassing a fermentation liquid which is supersaturated with carbon dioxide, they are not in equilibrium with the liquid environment and so the size of individual bubbles will increase as they rise towards the surface. Other methods are available for the formation of microbubbles from pressurized gas-saturated water.

When water is used as the gas-carrying liquid and oxygen, nitrogen or air is the gas, it is generally sufficient to dissolve the gas in the water in an amount equivalent to saturation at a pressure of about 5 atmospheres absolute pressure and a temperature of about 18° C. More gas may be dissolved in the water by lowering the temperature or increasing the pressure. For most purposes the temperature of water may be in the range 0° to 35° C and be saturated at a pressure in the range 2 to 15 atmospheres absolute pressure. It is, of course, not necessary to actually saturate the water (or other carrier liquid) at a given pressure or temperature of use. It may be desirable in some cases for instance to increase the hydraulic pressure of the liquid before delivery to the nozzle or other device used to form the microbubbles in order to improve the degree of shear imparted to the liquid. This is especially true if the gas used is somewhat more soluble than oxygen. Sufficient gas may be introduced, for instance, by saturating water with carbon dioxide at a pressure of about $\frac{1}{2}$ atmosphere above the pressure of the fermentation liquid at the level of delivery in the fermentation vessel, but in order to generate the microbubbles the water must be pressurized further to promote sufficient shear when it is passed through the nozzle.

It is only necessary to arrange for the controlled introduction of the high pressure gas-saturated liquid into the fermentation liquid via a needle valve or other nozzle. Excess $CO_2$ dissolved in the fermentation liquid will then be removed as the microbubbles grow and rise to the surface. The number of microbubbles generated is a linear function of the amount of high pressure gas-saturated liquid metered into the fermentation liquid and in consequence metering of this liquid enables a fairly close control to be maintained on the rate of removal of excess $CO_2$.

In a brewery fermentation it is often desirable to 'rouse' a fermentation in order to redistribute yeast that has separated from the bulk of the fermenting wort. The introduction of microbubbles at the base of the fermenting vessel will help to achieve the desired mixing since the passage of a cloud of $CO_2$ bubbles, formed on the microbubble nuclei, up the fermenting wort has a mild agitating effect on the wort bulk. A faster fermentation will be encouraged by this means and this benefit will be enhanced as a result of the lowering of the concentration of the carbon dioxide waste product of yeast metabolism. It may be desirable therefore to introduce microbubbles continuously during the vigorous phase of fermentation both from the point of view of holding down the supersaturation of the liquor by carbon dioxide and from the point of view of increasing the rate of fermentation.

At the end of primary fermentation it is sometimes the case in a brewery fermentation that the carbon dioxide level is undesirably high. This is most often the case when the fermentation is carried out in deep fermenters where the absolute pressure at the base of the fermenter may be as high as 3 atmospheres. At this pressure the $CO_2$ derived from the fermentation is not so readily flushed away during the fermentation. If the beer is then transferred and, for instance, filtered into a bright beer tank it is not unusual for the $CO_2$ content to remain too high for the product to be racked into keg or cask at the correct level of carbonation.

Treatment of the beer at any stage after primary fermentation to reduce $CO_2$ levels is possible with the technique of microbubble injection. The quantities of water injected for this purpose will be small, specifically less than 1% of the bulk volume in most cases. Nitrogen or carbon dioxide would normally be the preferred gas to use in this situation because oxidation of beer substances is otherwise possible and flavour changes may result.

A special feature of this invention is the way in which gas release from wort, beer or other fermentation liquids is controlled. In effect, the invention speeds up the natural release of gas from a supersaturated liquid by introducing a controllable quantity of microbubbles. Other methods such as gas bubbling are both inefficient in their use of gas and tend to cause uncontrolled release of dissolved gas due to introducing a degree of turbulence into the fermentation liquid which is sufficient to trigger off the growth of incipient gas bubbles on other nuclei throughout the bulk of the fermentation liquid.

The following examples of the invention are given.

EXAMPLE 1

High pressure oxygenated water is used to oxygenate a fermenter containing yeast and wort. A tank containing water saturated with oxygen at a partial pressure of 5 atmospheres supplies liquid to the fermenter which is at or near atmospheric pressure. The liquid flow is controlled by a valve in the supply line to the fermenter and by an injector in the base of the fermenter. In a simple form the injector can comprise a short length of narrow bore tubing so that almost the whole of the pressure drop occurring between the water tank and the fermenter takes place down the length of the tube and only occupies a fraction of a second in time. The jet of water injected into the fermenter in this manner is vigorous enough to cause rapid mixing of the oxygenated water and the wort in the fermenter. It is calculated that 5 atmospheres absolute pressure and 2° C the water will contain sufficient oxygen to introduce 6 ppm oxygen into the fermenter when injected in an amount of 2% of the volume of the wort wool, 6 ppm oxygen being a typical figure for dissolved oxygen in a brewery wort at the start of fermentation.

EXAMPLE 2

Water saturated with oxygen at 10 atmospheres pressure and at 2° C is metered into an external circulation line from a brewery fermenter. The line is maintained at 10 atmospheres absolute pressure in a section where the fluid streams meet and turbulence is encouraged in this section so that good mixing is achieved. The mixed fluids are then returned to the fermenter via a pressure relief valve to reduce the pressure to that of the fermenter. The two fluids are mixed in line in the proportion of 1 part of oxygenated water to 9 parts of fermentation liquid.

EXAMPLE 3

Water saturated with oxygen at 5 atmospheres pressure and at 2° C is introduced into a pipeline containing oxygen-free brewery wort at about 18° C on its way to a fermenter. The water is metered in at 2% of the rate of wort flow via an injector as described in Example 1 and is rapidly mixed with the wort. The pressure in the pipeline at this point may be at any suitable value between 1 and 5 atmospheres absolute pressure.

EXAMPLE 4

A supply of water is held in a tank at an absolute pressure of 10 atmospheres. This water is saturated at 2° C with nitrogen. This gas-containing liquid is then metered into a pipe line containing a flow of beer on its way to a storage tank. The mixing of the liquids may be achieved as in Example 3, except that the line pressure may be as high as 10 atmospheres absolute pressure. A suitable dilution rate for this process would be 5%.

Where fermentation liquids such as brewery wort are concerned, oxygenated water may be added either direct to the fermentation vessel, or to the wort as it passes to the fermentation vessel or to wort which is re-circulated from and back to the fermentation vessel. The last alternative may in some instances have the disadvantage that the recirculation of the wort encourages the formation of carbon dioxide bubbles which strip oxygen from the oxygenated water either as the two are passed together to the fermenter or after injection thereinto. Carbon dioxide release could in fact be rather violent if the recirculation is started at a stage when the dissolved carbon dioxide level is high. Also, in these circumstances it may be found to be difficult to inject carrier liquid directly into a fermentation without similarly causing excessive spontaneous release of dissolved carbon dioxide.

The sudden release of dissolved carbon dioxide can be avoided by recirculating the wort continuously during the fermentation period substantially as in Example 2, but starting at a time when the level of dissolved carbon dioxide is still low enough to avoid the triggering of excessive sudden fobbing. Oxygenated water may then be added into the recirculation line or directly to the bulk of the fermenting wort without significantly changing the rate at which dissolved carbon dioxide is released.

The triggering of rapid release of dissolved carbon dioxide from a fermentation may be avoided, as already explained, by the introduction of gas microbubbles. Thus, if a fermenting wort is first subjected to this treatment to sufficiently reduce the level of dissolved carbon dioxide it is then possible to inject oxygenated water directly or indirectly into the wort in the fermentation vessel, substantially by the methods described in Examples 1 and 2 for instance, without fear of initiating sudden over-fobbing. It is convenient and generally practical in such a case to use a common supply of oxygenated water for degassing purposes and for the main oxygen injection itself. On occasion, however, it may be preferred to use separate supplies in which case it is possible to use nitrogen or other suitable gas as the source of the microbubbles if the introduction of oxygen during the degassing period is not desired.

In yet another method the carrier liquid (e.g. oxygenated water) is introduced directly into the fermentation liquid via a nozzle which is designed such that the velocity of the stream of carrier liquid entering the fermentation liquid is relatively low when compared with, for example, the velocity of the liquid emerging from a short length of tube in the manner described in Example 1. A low velocity stream of carrier liquid may be achieved in a variety of ways but it is common to all these methods that the pressure energy contained in the carrier liquid at the point of entry to the nozzle is absorbed gradually by the nozzle without inducing sudden lowering in the pressure, whether localized or general, at any stage in the passage of the carrier liquid through the nozzle. If this condition is met then it is possible to reduce the pressure on the carrier liquid without initiating the growth of an excessive number of gas bubbles during its passage through the nozzle. Indeed, if the degree of supersaturation is not too high it is possible to deliver the carrier liquid into the fermentation liquid without any visible bubble formation in the carrier liquid stream whatever.

Reference is now made to the accompanying drawings, in which.

Figure 1:
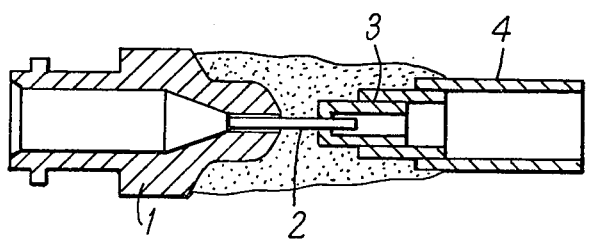
FIG. 1 is a section of one form of nozzle for the generation of microbubbles.

In FIG. 1 the supersaturated oxygen, nitrogen or air solution is passed through a hypodermic needle fitting 1 so as to pass through a restricted passage 2, from which it is injected to passages 3, 4 of progressively greater diameter.

Water, saturated at 18° C and 5 atmospheres pressure with nitrogen is allowed to pass through this device down a shortened hypodermic needle which has been modified by the addition of short sections of progressively wider bore stainless steel tube. The effect of sudden alteration in the diameter of the tube down which the gas-saturated water is travelling at high velocity is such as to cause a sudden drop in pressure which triggers off the release of microbubbles. These are probably formed on incipient bubble nuclei already present in the water.

It is estimated that under these conditions greater than 100,000 microbubbles are produced in every milliliter of water expelled from the nozzle. The flow rate of this nozzle is 40 ml/minute. Several million microbubbles can therefore be introduced to a fermentation over a short time period.

Figure 2:
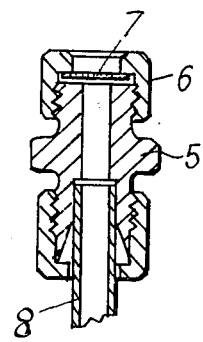
FIG. 2 is an alternative form of nozzle for the same purpose.

The degassing nozzle shown in FIG. 2 was constructed from a ¼ inch internal diameter straight brass pipe fitting 5 with a brass cap nut 6 having a 5/16 inch bore hole in the centre and screwed down onto a disc of sintered fibre stainless steel sheet 7 (Dynalloy X3, manufactured by Fluid Dynamics Incorporated, New Jersey, U.S.A.).

When water saturated with oxygen gas at 4 atmospheres pressure and 18° C was passed through the fitting via ¼ inch outside diameter stainless steel tube 8 it emerged at atmospheric pressure as a milky liquid containing a multitude of microbubbles. The flow rate was 1.24 liters/min. in this case.

Figure 3:
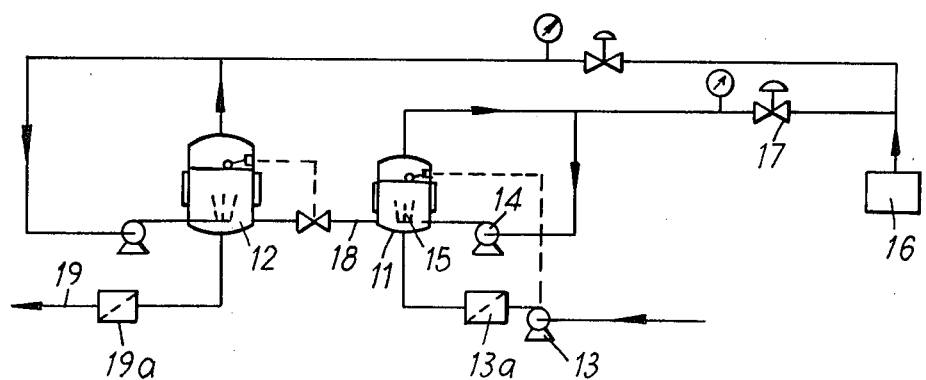
FIGS. 3 and 4 show schematically systems for the introduction of oxygen into a fermentation liquid.
Figure 4:
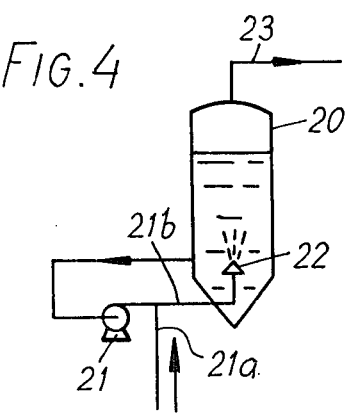

FIGS. 3 and 4 of the accompanying drawings show schematically two forms of apparatus which may be used in certain aspects of the present invention.

From the foregoing it will be appreciated that it will be possible to operate a brewery using normal and/or high specific gravity fermentation in which all the oxygen used in the fermentations is supplied from a single oxygenated water plant wherein the carrier water is oxygenated. Such a plant would be relatively small and cheap and could be operated on a substantially permanent basis to provide oxygen as and when required to the various fermentation vessels.

FIG. 3 shows a possible form of oxygenating plant schematically to have first and second oxygenating vessels 11 and 12 respectively, typically stainless steel pressure vessels. Water at 2° C will enter the first vessel 11 via a pump 13 and a coarse filter 13a to be oxygenated, typically by a sparging system involving a closed circuit with a pump 14 and nozzle 15 connected to an oxygen supply 16 via a valve 17. This first vessel 11 may be operated at for instance 10 atmospheres and the oxygenated water will then be passed via line 18 to the second vessel 12 which may be operated at a lower pressure, for instance 5 atmospheres at the same temperature of 2° C. A similar type of sparging system involving a pump, nozzle and closed circuit is associated with the second vessel 12 and connected to the oxygen supply 16. Provided the withdrawal of water to the fermenters through a line 19, including a sterilizing filter 19a, is not excessive then the oxygen content of the water in the second vessel 12 will remain constant as the feed from the vessel 11 will be supersaturated with respect to the second vessel 12. Accordingly, oxygenation of worts or other fermentation liquids can therefore be accurately controlled.

Addition of the oxygenated carrier water must be accomplished correctly in order to avoid bubble formation. As has been mentioned, this may be achieved by rapid dilution of high pressure oxygenated water into the fermentation liquid so that insufficient time is allowed for bubble formation or by dilution at high pressure before releasing the mixture to atmospheric pressure. In the former case the addition may be in line or directly into the fermenter through a nozzle of the type shown in FIG. 5, whereas in the latter case the addition must be in line but could accommodate oxygenated water equilibrated at higher pressure.

FIG. 4 shows schematically a simple system for oxygenating fermentation liquid in a fermenter before or during fermentation in a fermentation vessel as shown at 20 typically maintained at 1 atmosphere pressure. Fermentation liquid is circulated via pump 21 on the downstream side of which is a connection 21a to a supply (not shown, but which could be as shown in FIG. 3) of oxygenating carrier water which might be at 5 atmospheres. It is possible for four volumes of recirculated fermentation liquid to take one volume of the oxygenated water. A nozzle 22, provided adjacent to the base of the vessel, allows high pressure injection of the mixed fermentation liquid and oxygenated water. This nozzle may conveniently be designed to open at a set pressure, for instance 5 atmospheres.

As the gas content of the mixed fermentation liquid and oxygenated water will be less than the saturation level of dissolved gas at the pressure in line 21b there will be little tendency for oxygen to come out of solution if this system is employed. In a beer fermentation this is especially true if the recirculation system is run from an early stage in the fermentation so as to avoid sudden release of dissolved carbon dioxide when the oxygenation is started. The changes of triggering sudden excessive release of carbon dioxide will be further reduced if the nozzle 22 is of a type that minimizes turbulence such as, for example, that shown in FIG. 5.

Alternatively, it is satisfactory to reduce the level of dissolved carbon dioxide in the fermenting wort by a sufficient degree to prevent excessive sudden fobbing from occurring when the recirculation system is started. This prior treatment of the fermenting wort may be achieved by using the technique of controlled introduction of microbubbles.

In brewery fermentations of wort is is common to collect the carbon dioxide from closed fermentation vessels and this gas will be drawn off from the tops of the vessels. This is indicated in FIG. 4 where carbon dioxide is shown as being taken from vessel 20 via line 23.

It will be appreciated that the invention provides a method whereby small amounts of relatively insoluble gas may be delivered quantitively to fermentation liquid in such a way that little or none of the relatively insoluble gas ever appears in the fermentation liquid as bubbles. This is expected to be of particular advantage to brewers wishing to dissolve accurate quantities of oxygen in worts both before and during fermentation enabling more accurate control of fermentations in respect of yeast growth during fermentation and the balance of flavour compounds in the finished beer. The method proposed is economical, simple and accurate, largely eliminating wastage of introduced gas, reducing foam formation and contamination of collected carbon dioxide.

The effectiveness of the microbubble technique for controlling the level of carbon dioxide is illustrated by the following additional example.

EXAMPLE 5

Eight barrels of a typical strong ale wort (S.G.1080.6) were collected in a cylindro-conical fermenting vessel at 64° F. This wort was pitched with a brewery strain of S.cerevisiae at a rate of $6 \times 10^6$ cells/ml. The wort was allowed to ferment normally for 14½ hours, during which time the dissolved $CO_2$ content of the wort was measured and observed to rise to 1.3 vols. At this time, decarbonation was commenced by means of microbubble injection using oxygen-saturated water at a pressure of 11 atmospheres (absolute) and at a temperature of 3° C. The water was transmitted to the wort at regular intervals by passage through a nozzle of the type illustrated in FIG. 1. This nozzle had a flow rate of 57 ml/min. The duration of each injection, and also the interval between injections, was controlled automatically by a two-position valve in the water line which was linked to an adjustable timer. For example, to give an overall injection rate of 470 ml/hr the system was set to deliver water for approximately 25 seconds in every 3 mins.

Further measurement of the dissolved $CO_2$ level showed that decarbonation was effective. This procedure was continued for 12½ hours at varying injection rates and the $CO_2$ content of the wort was thereby controlled at 1.1 ± 0.05 vols. during this period despite an increasing rate of fermentation. The total dilution of the wort during this period was 0.62%, representing a reduction in the O.G. of about 0.5°. Details of this experiment are given in Table 1.

Table 1.

| Time from pitching | Specific gravity | Temp. (° F) | Water injection rate (ml/hr) | Dissolved $CO_2$ (vols) |
|---|---|---|---|---|
| 0 | 1080.6 | 64 | — | — |
| 5 | 1079.8 | 64 | — | 0.35 |
| 8½ | 1079.2 | 64 | — | 0.85 |
| 11½ | 1078.5 | 64.5 | — | 1.15 |
| 14 | 1077.5 | 65 | — | 1.30 |
| 14½ | — | — | 470 | — |
| 15½ | 1076.8 | 65 | 470 | 1.10 |
| 17 | 1075.9 | 65.5 | 470 | 1.05 |
| 19½ | 1074.0 | 66.5 | 470 | 1.10 |
| 21 | 1072.5 | 67 | 470 | 1.15 |
| 21½ | — | — | 705 | — |
| 22½ | 1070.8 | 67 | 705 | 1.10 |
| 24 | 1068.7 | 67 | 705 | 1.10 |
| 25½ | — | — | 1410 | — |
| 27 | 1062.6 | 66.5 | 1410 | 1.10 |

Figure 5:
FIG. 5 shows a form of nozzle for introduction of oxygenated water without generation of microbubbles.

In a system where it is desired to control both the oxygen content of wort and the dissolved $CO_2$ level, parallel injector nozzles of the type illustrated in FIGS. 1 and 2 for microbubble generation and of the type illustrated in FIG. 5 for quiet oxygenated water injection would be provided at the bottom of the fermenter with appropriate valving to allow a selected nozzle to be employed. Oxygenated water may be introduced through the appropriate nozzle according to which operation is desired, i.e., oxygenation or degassing. Where the level of dissolved $CO_2$ is low, it is possible to introduce the oxygen via a microbubble-generating injector nozzle, but this is not generally a convenient operation.

I claim:

1. A method of oxygenating brewers' wort during fermentation which consists of introducing into said wort a solution of oxygen or air in an aqueous carrier liquid selected from the group consisting of water, brewers' wort and beer, said solution being introduced into said wort at a predetermined depth, at a higher pressure than the pressure at said predetermined depth and under conditions such that the oxygen or air is retained in solution in the wort, said solution being super-saturated with oxygen or air at the temperature and under the pressure of the wort at said predetermined depth, the volume of said oxygen or air solution introduced during a single fermentation being not more than about 5% of the bulk volume of said wort in said fermentor.

2. A method of degassing brewers' wort during fermentation or degassing fermented beer, said wort or beer being supersaturated with carbon dioxide, which method comprises
    1. dissolving a gas selected from the group consisting of oxygen, nitrogen, carbon dioxide and a mixture thereof in an aqueous carrier liquid selected from the group consisting of water, brewers' wort and beer to form a solution which is saturated with said gas at a superatmospheric pressure, and
    2. introducing said solution into said wort or beer at a predetermined depth, under conditions leading to a high degree of shear thereby causing said gas to be liberated from said supersaturated solution as a multitude of microbubbles, said multitude of microbubbles being characterized by a distinctive milky appearance, said solution becoming supersaturated with said gas under the temperature and pressure of said wort or beer at said predetermined depth.

3. A method according to claim 1, wherein said solution is a solution of oxygen in water.

4. A method according to claim 1, wherein said solution is mixed with a portion of said wort at a pressure higher than the pressure at said predetermined depth, and the resultant mixture is then introduced into the bulk of the wort.

5. A method according to claim 4, wherein a stream of the wort is withdrawn from the bulk of said wort, said wort stream is mixed with a stream of said solution, and a stream of the resultant mixture is then introduced into the bulk of said wort at said predetermined depth.

6. A method according to claim 1, wherein said wort is supersaturated with carbon dioxide.

7. A method according to claim 1, wherein said gas is oxygen and/or nitrogen, and said gas is dissolved in said carrier liquid under a pressure of at least 3 atmospheres and at a temperature below 25° C.

8. A method according to claim 7, wherein said gas is dissolved in said carrier liquid under a pressure of 5–10 atmospheres and a temperature of 2°–18° C.

9. A method according to claim 1, wherein said solution is injected intermittently into said wort or beer to control the number of nuclei-forming microbubbles generated therein.

10. A method according to claim 1, wherein the volume of said solution introduced into said wort or beer is not more than about 1% of the volume of said wort or beer.

* * * * *

UNITED STATES PATENT OFFICE
CERTIFICATE OF CORRECTION

Patent No. 4,041,180           Dated August 9, 1977

Inventor(s) Richard John Hugh Wilson

It is certified that error appears in the above-identified patent and that said Letters Patent are hereby corrected as shown below:

In claims 7, 9 and 10, line 1 of each, change "1" to --2--.

Signed and Sealed this

Thirtieth Day of September 1980

[SEAL]

*Attest:*

SIDNEY A. DIAMOND

*Attesting Officer*     *Commissioner of Patents and Trademarks*